US00PP27179P2

(12) United States Plant Patent
Shepherd et al.

(10) Patent No.: US PP27,179 P2
(45) Date of Patent: Sep. 20, 2016

(54) ***SOLENOSTEMON* PLANT NAMED 'MONKEY ISLAND'**

(50) Latin Name: *Solenostemon scutellarioides*
Varietal Denomination: Monkey Island

(71) Applicant: Memphis Zoo, Inc., Memphis, TN (US)

(72) Inventors: Connie Shepherd, Memphis, TN (US); Jill Maybry, Memphis, TN (US)

(73) Assignee: Connie Shepherd, Memphis, TN (US)

( * ) Notice: Subject to any disclaimer, the term of this patent is extended or adjusted under 35 U.S.C. 154(b) by 91 days.

(21) Appl. No.: 13/999,524

(22) Filed: Mar. 6, 2014

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Baker, Donelson, Bearman, Caldwell & Berkowitz, PC; Cong Ding

(57) ABSTRACT

A new and distinct *Solenostemon* plant named 'Monkey Island', characterized by its vigorous, upright growth habit, the width of its leaves measuring at about 5 cm, and its foliage pattern of splotches of maroon, medium green, green, white, pink, and red.

2 Drawing Sheets

Latin name of genus and species of plant claimed: *Solenostemon scutellarioides.*

Variety denomination: 'Monkey Island'.

STATEMENT REGARDING FEDERALLY-SPONSORED RESEARCH

None.

BACKGROUND OF THE INVENTION

The presently-disclosed invention relates to a new and distinct cultivar of *Solenostemon* plant botanically knows as *Solenostemon scutellarioides* and hereinafter referred to by the cultivar name 'Monkey Island'.

The new cultivar 'Monkey Island' was discovered in the gravel immediately under the germination beds in the Memphis Zoo East Greenhouse of Memphis, Tenn. in March 2012. The parents of the cultivar are unknown at this time.

Asexual reproduction of the new cultivar has been conducted by terminal stem cuttings since March 2012. It has been demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Monkey Island' as a new and distinct cultivar of *Solenostemon* plant:

1. Foliage pattern resembles an artist's palette: mixed splotches of maroon, medium green, green, white, pink, and red.
2. Leaf margins are gently scalloped by 5 cm.
3. Vigorous, upright growth habit.

Of the many commercially available *Solenostemon* cultivars, a similar cultivar is Painted Nettle 'Careless Love' (not patented). However, in side by side comparisons, plants of the new cultivar, 'Monkey Island', differ in the following characteristics:

Plants of the new cultivar have a foliage color difference in that 'Careless Love' has two colors and 'Monkey Island' exhibits up to six colors per leaf.

Plants of the new cultivar have a more deeply scalloped leaf margin by 2 cm than plants of 'Careless Love'.

BRIEF DESCRIPTION OF THE PHOTOGRAPHS

The accompanying photographs show, as nearly true as it is reasonably possible to make the same in color illustrations of this type, and typical foliage characteristics of the new cultivar. Colors in the photographs differ slightly from the color values sited in the detailed description, which accurately describes the colors of 'Monkey Island'. The plants were grown in 6 flats of 1801s for 12 weeks in a greenhouse and later planted in several locations throughout the Memphis Zoo in Memphis, Tenn. The age of the plant is four months.

DETAILED BOTANICAL DESCRIPTION

Figure 1:
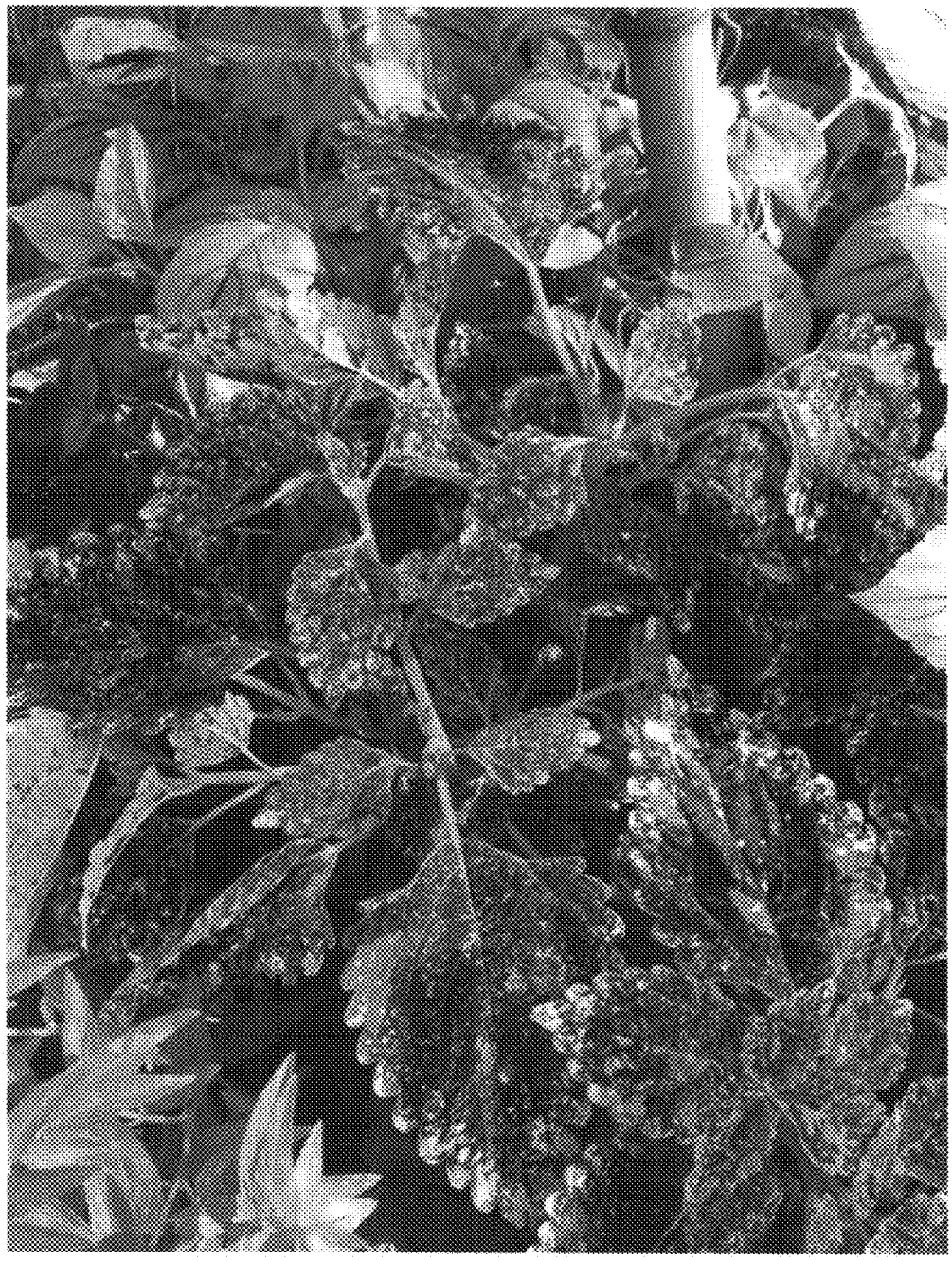
FIG. 1 illustrates a view of the overall growth and habit of 'Monkey Island' in container at Memphis Zoo Greenhouse.
Figure 2:
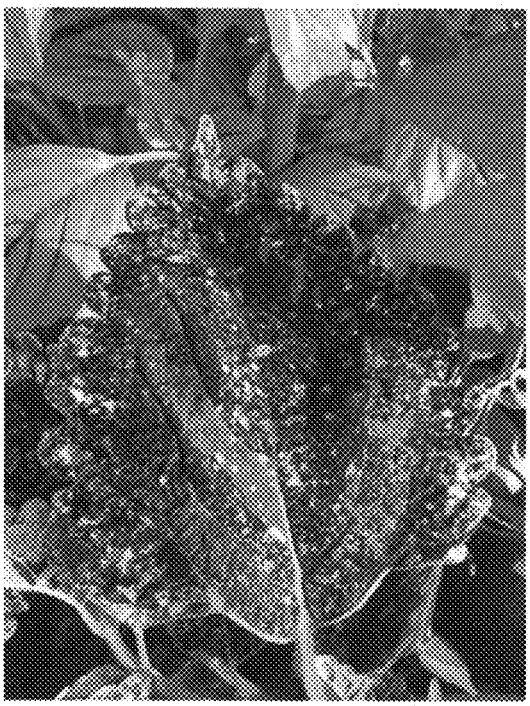
FIG. 2 illustrates a close-up view of an individual leaf of 'Monkey Island'.

The new cultivar has been observed in a greenhouse setting and outside environment. Accordingly, it is possible that the phenotype may vary somewhat with variations in the environment, such as temperature, light intensity and day length without any variance in the genotype. The age of the plant is four months.

The chart used in the identification of colors described herein is The R.H.S. Colour Chart of The Royal Horticultural Society, London, England, 2001 edition, except where general color terms of ordinary significance are used. The color values were determined under natural light conditions in Memphis, Tenn. on Jan. 28, 2014 between 1:00 p.m. and 3:00 p.m.

The following descriptions and measurements describe plants produced from cuttings from the original stock plant and grown in a glass-covered greenhouse under conditions comparable to those used in commercial practice. The plants were grown in Memphis, Tenn. in six flats of 1801s for 12 weeks utilizing a soilless growth medium (Fafard 3B). Greenhouse temperatures were maintained at 60 degrees F. to 70 degrees F. (15.6° C. to 21.1° C.) during the day and approximately 55 degrees F. to 60 degrees F. (12.8° C. to 15.6° C.) during the night. Measurements and numerical values represent averages of typical plants.

Botanical classification: *Solenostemon scutellarioides* cultivar 'Monkey Island'.

Parentage: Unknown.

Propagation:

*Type cutting*.—Terminal stem.

*Time to initiate roots*.—Approximately 4 to 10 days.

*Time to produce a rooted cutting*.—Approximately 22 to 25 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Vigorous, upright.

*Size*.—Plant Height: From soil level to top of plant plane: Approximately 76.2 cm. Plant Width: Approximately 48.9 cm.

*Branching habit*.—Freely branching, pinching improves basal branching.

*Quantity of lateral branches per plant*.—Approximately 9.

*Branch*.—Strength: Strong. Shape: Square in cross section. Length of lateral branch: Approximately 12.9 cm. Diameter of lateral branch at central internode: Approximately 5.5 mm. Length of central internode of lateral branch: Approximately 3.5 cm. Texture: Densely pubescent with short hairs. Color of young and mature stems: N77D.

Foliage description:

*General description*.—Quantity of leaves per main stem: Approximately 8. Fragrance: None. Form: Simple. Arrangement: Opposite.

*Leaves*.—Aspect: Petiole is at an acute angle to stem; leaf blade transitions to an obtuse angle with age. Shape: obovate. Margin: Scalloped. Apex: Mucronate. Base: Truncate. Venation pattern: Pinnate. Length of mature leaf: 11.2 cm. Width of mature leaf: 6.1 cm. Texture of upper surface: Sparsely pubescent. Texture of lower surface: Sparsely pubescent with dense pubescence on venation. Color of upper surface of young foliage: Irregular distribution of 59A, 53A, 2C, and 145A looking like a painter's palette. Color of lower surface of young foliage: Irregular distribution of 59A, 53A, 2C, and 145A looking like a painter's palette. Color of upper surface of mature foliage: Irregular distribution of 59A, 53A, 2C, 145A, 61C, and 91D looking like a painter's palette. Color of lower surface of mature foliage: Irregular distribution of 59A, 53A, 2C, 145A, 61C, and 91D looking like a painter's palette. Venation is indistinguishable from lamina.

*Petiole*.—Length: Approximately 4.5 cm. Width: Approximately 2.0 mm. Texture: Densely pubescent. Color: N77D.

Flowering description: Flowers are ornamentally insignificant for this variety. They are pinched off to keep the plant from going to seed and to create a bushier look for the plant. Flowers observed were on a stalk 8 cm long. The florets were opposite. Color: 97A.

Seed and fruit production: Neither seed nor fruit production has been observed.

Disease, and pest resistance: Resistance to pathogens and pests common to *Solenostemon* has not been observed.

Cold hardiness: The plant described as 'Monkey Island' is best grown as an annual for its color. It is hardy in Zone 9 down to 50 degrees.

What is claimed is:

1. A new and distinct cultivar of *Solenostemon* plant named 'Monkey Island', substantially as herein illustrated and described.

* * * * *